United States Patent [19]

Deaton

[11] Patent Number: 4,935,679

[45] Date of Patent: Jun. 19, 1990

[54] ELECTRO MECHANICAL INTERFACE FOR AUTOMATING ANALYTICAL INSTRUMENTS

[76] Inventor: Chris D. Deaton, 3705 Government St., Ocean Springs, Miss. 39531

[21] Appl. No.: 226,803

[22] Filed: Aug. 1, 1988

[51] Int. Cl.⁵ .............................................. H02F 1/00
[52] U.S. Cl. ................................. 318/491; 250/522.1
[58] Field of Search ............... 318/491, 566, 626, 640, 318/647, 664, 538, 550, 552, 466, 467, 468; 250/522.1, 224; 248/429, 394

[56] References Cited

U.S. PATENT DOCUMENTS

| | | | |
|---|---|---|---|
| 2,997,591 | 8/1961 | Guentner et al. | 250/522.1 |
| 4,628,523 | 12/1986 | Heflin | 250/522.1 |
| 4,777,610 | 10/1988 | Barwick et al. | 250/224 X |

FOREIGN PATENT DOCUMENTS 188035 11/1983 Japan ................................. 250/522.1

OTHER PUBLICATIONS

X-Ray Polycrystalline Diffraction II Program Description and Operations, Program No. 5798-RLP, pp. 73-76.
Omni-Computer, Brochure, 1987.

Primary Examiner—William M. Shoop, Jr.
Assistant Examiner—A. Jonathan Wysocki
Attorney, Agent, or Firm—Alexander F. Norcross

[57] ABSTRACT

A planar bracket for demountably affixing an incrementally controlled motor for a manually settable x-ray diffractometer. A gear pully and driver are operably interconnected to rotate the instrument axis. Two interrupters are utilized to sense an occurrence of a limit pin as well as a direction of travel.

3 Claims, 6 Drawing Sheets

ELECTRO MECHANICAL INTERFACE FOR AUTOMATING ANALYTICAL INSTRUMENTS

BACKGROUND OF THE INVENTION

This invention relates to laboratory x-ray instruments used to analyze the chemical compositions of compounds and elements, and other material, specifically by means of x-ray diffraction or fluorescence.

A well known method of analyzing the physical composition of a chemical compound or element or of a material, including crystalline materials, is by means of obtaining a profile of the material's reflectance or fluorescence under x-rays. Such a profile is produced by obtaining a series of data points, at various angles of reflection, of the intensity by which the material reflects x-rays or fluoresces when illuminated at various angles by an x-ray source.

Prior art instruments for x-ray analysis, for example, a typical Philips-Norelco X-ray Diffractometer, utilize a motor-driven worm gear to rotate a material about a first axis and an arm supporting a detector, both rotated in a coordinated manner through a given arc, periodically stopping to obtain readings of the intensity of the x-ray reflectance or fluorescence at various angles. For this reason, a dial display is provided upon the instrument to indicate the relative angular position of the sample. The instrument, in simplest form, then comprises a motor, some form of mechanical input to allow prepositioning of the sample; and a clutch assembly connecting the motor drive to a worm gear driven, indexed sample holding axis and detector positioning means.

Prior attempts have been made to automate such a device in order to eliminate the manual steps of setting the sample at various angles, manually reading the angle off the index scale, and recording x-ray intensity.

A typical method, for instance, as shown in International Business Machines (IBM) Corporation's *X-ray Polycrystalline Diffraction II Program Description and Operations Manual*, SBa30-1956-0 (undated), is to disassemble the diffraction instrument, gaining access to the clutch mechanism internal to the instrument. The clutch mechanism is then either removed or drilled so as to be pinned to prevent clutch slippage, rendering the clutch permanently inoperable. A computer driven motor or incrementally controlled motor is permanently mounted for driving through the fixed clutch. This technique usually requires the custom design of a motor housing in order to hold the motor and the clutch mechanism in alignment. It may be necessary to spring-mount the motor so as to prevent binding between the shafts, even though there is a consequent loss of precision of angular motion of the motor.

Once made, such modification renders the instrument unusable for further manual operation, and further so affects the entire instrument that it must be reassembled and realigned with the x-ray tube. This is a mechanical realignment that can only be performed by a highly trained, experienced analytical x-ray instrument technician and it results in significant downtime whenever an instrument is so configured.

SUMMARY OF THE INVENTION

The current invention discloses a mount and adaptor mechanism for providing direct incrementally controlled motor control of an existing manual/motor driven x-ray instrument.

The necessity for disassembly or modification to the interior of the instrument is eliminated by providing a front mount bracket which may be conveniently, but removably, affixed to the instrument. The bracket supports a incrementally controlled motor, with appropriate computer interconnection, operating a belt or chain drive, optionally tensioned by an idler mechanism, which in turn is conveniently connected to the instrument by removing the manual or clutch shaft gear, adjacent to the manual control knob, replacing it with a selected driven pulley or gear, mating to the belt or chain drive.

The modification thus preserves the action of the clutch, requires no invasive modifications to the instrument and does not disturb the instrument alignment or calibration.

The invention further comprises a removable positioning arc, adapted to be readily fastened to an existing positioning linkage on the instrument, containing movable limit pins which interconnect with an optical sensor on the front mount bracket so as to permit the ready setting of maximum and minimum angular excursion limits of the instrument. This latter provides a precise feedback mechanism to a computer control for detecting inadvertant overrun of the angular limits beyond which the machine should not progress. These limits being established, the incrementally controlled motor can be exactly controlled by computer controls in a manner well understood in the art, the ratio of incrementally controlled motor movement to machine movement being defined by preselected gear or pulley ratios, with the extreme indexes as backup safety limits; the exact positioning between indexes can also be computer determined and controlled.

This permits the ready adaption of a manual or analogue x-ray instrument to direct computer control, including computer collection of x-ray diffraction data to as fine a degree as can be desired.

It is thus an object of the invention to provide for a ready modification technique for existing x-ray diffraction instruments that can be easily installed and removed by the user without the necessity of recalibrating or modifying the interior of the basic x-ray diffraction instrument.

It is a further object of this invention to provide the modification to an x-ray instrument to permit use of a computer control that can be easily moved from one x-ray instrument to another.

It is a further object of this invention to provide a method of automating an existing x-ray instrument which does not mechanically alter the internal mechanism of the instrument.

It is a further object of this invention to provide a modification to an x-ray instrument permitting computer control which does not inhibit manual operation of the x-ray instrument.

It is a further object of this invention to provide a modification permitting computer control of an x-ray instrument which minimizes downtime during the conversion process and obviates the necessity of recalibration or the presence of a trained instrumentation technician for the performance of the modification.

It is a further object of this invention to provide a that provides all necessary signals and limit indications through a single connector for uniform computer control.

These and other objects of the invention may be clearly seen from a detailed description of the preferred embodiment which follows:

DETAILED DESCRIPTION OF THE PREFERRED EMBODIMENT

Figure 1:
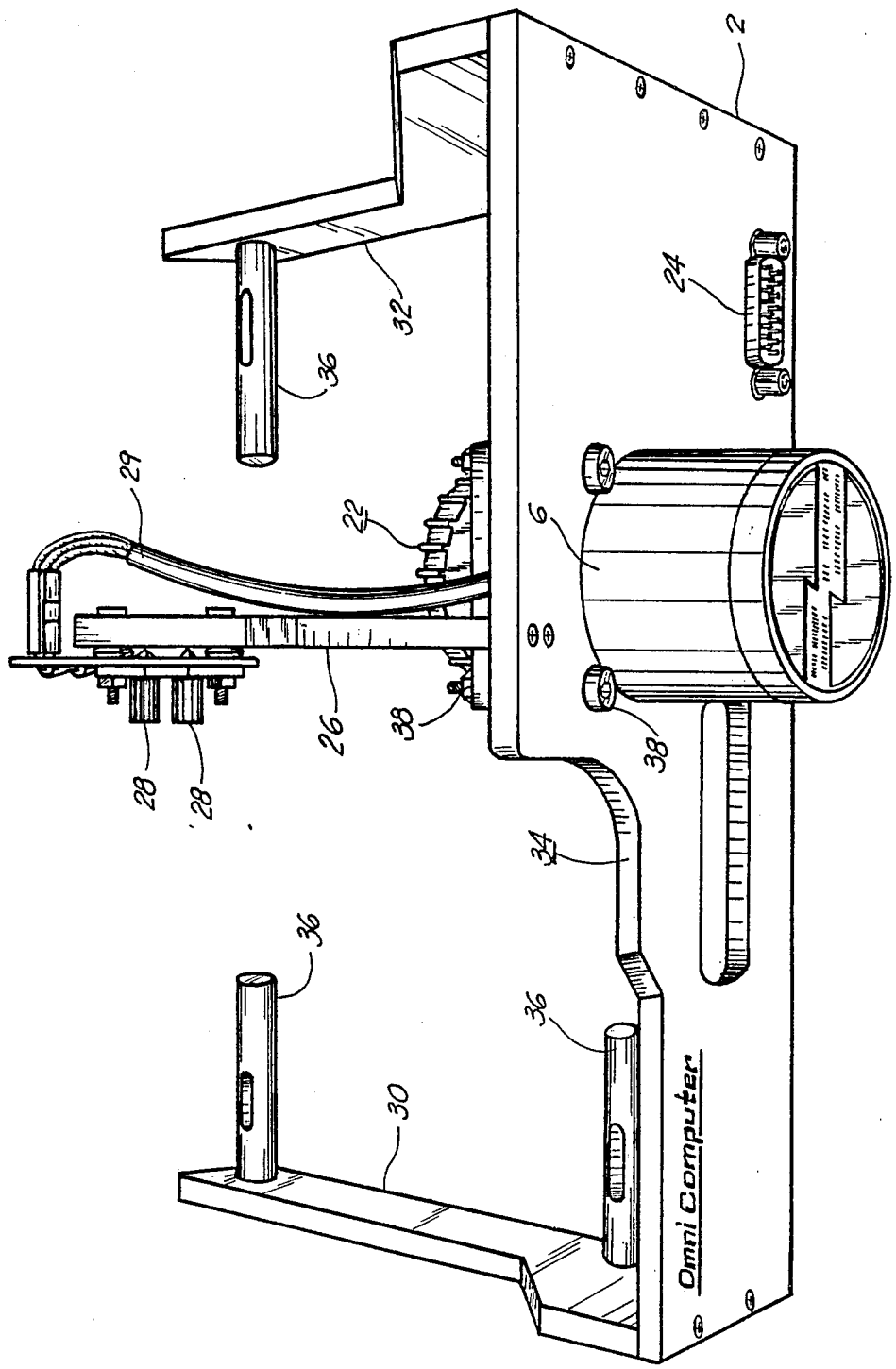
FIG. 1 is a view of the demountable bracket of the invention.
Figure 2:
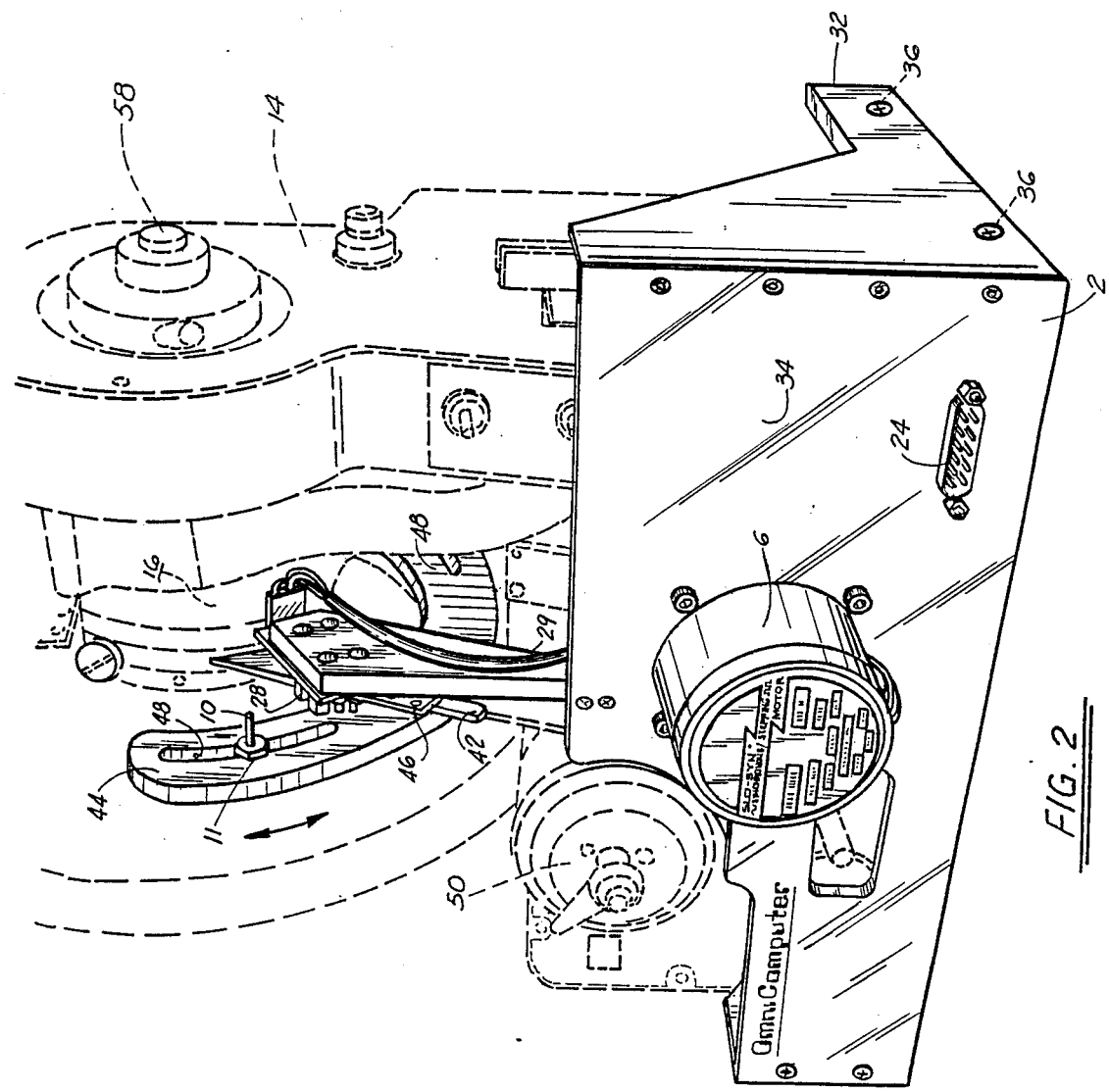
FIG. 2 is a view of the invention, as installed upon an x-ray instrument prior art.
Figure 3:
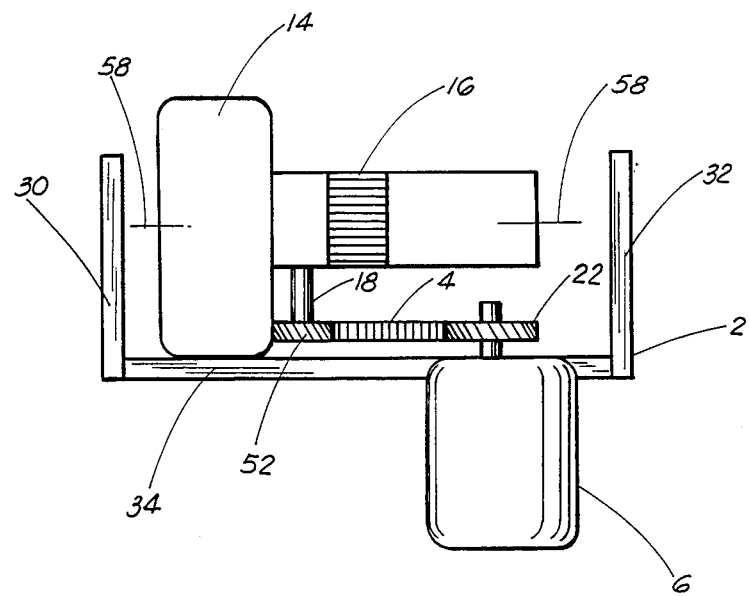
FIG. 3 is a top view of the invention, operatively interconnected to the instrument.
Figure 4:
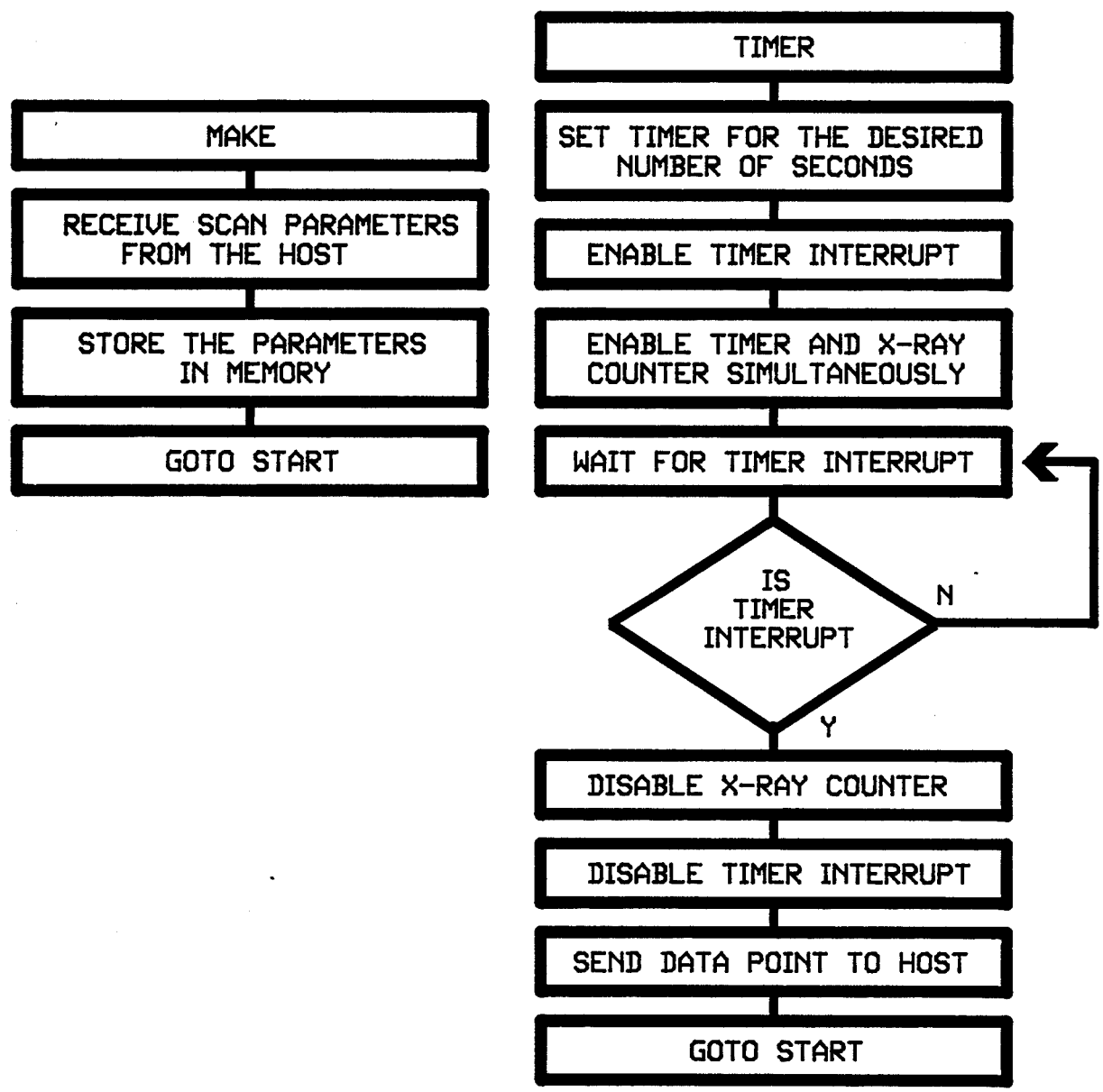
FIGS. 4–6 are flow charts depicting a typical Computer Control of the instrument.
Figure 5:
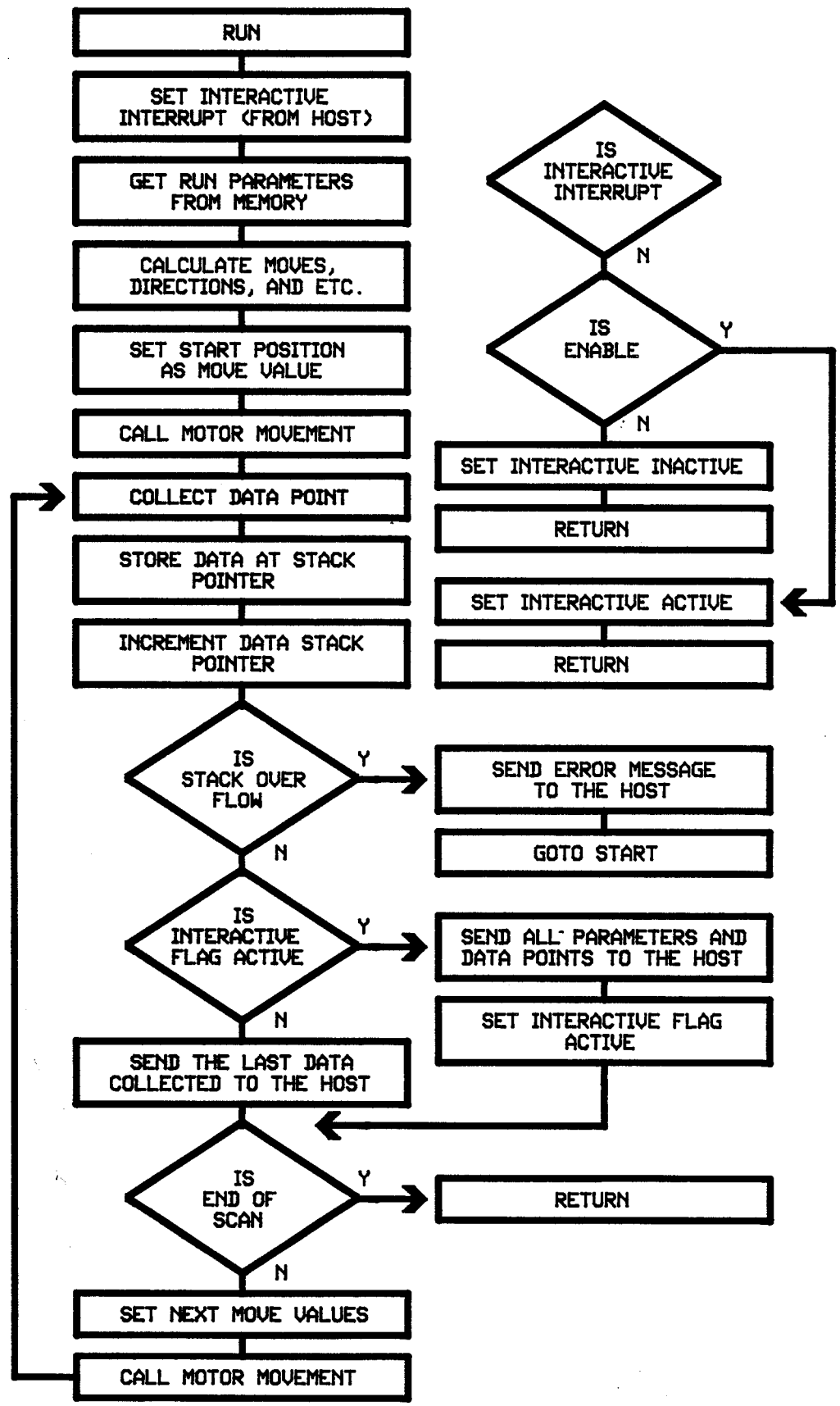
Figure 6:
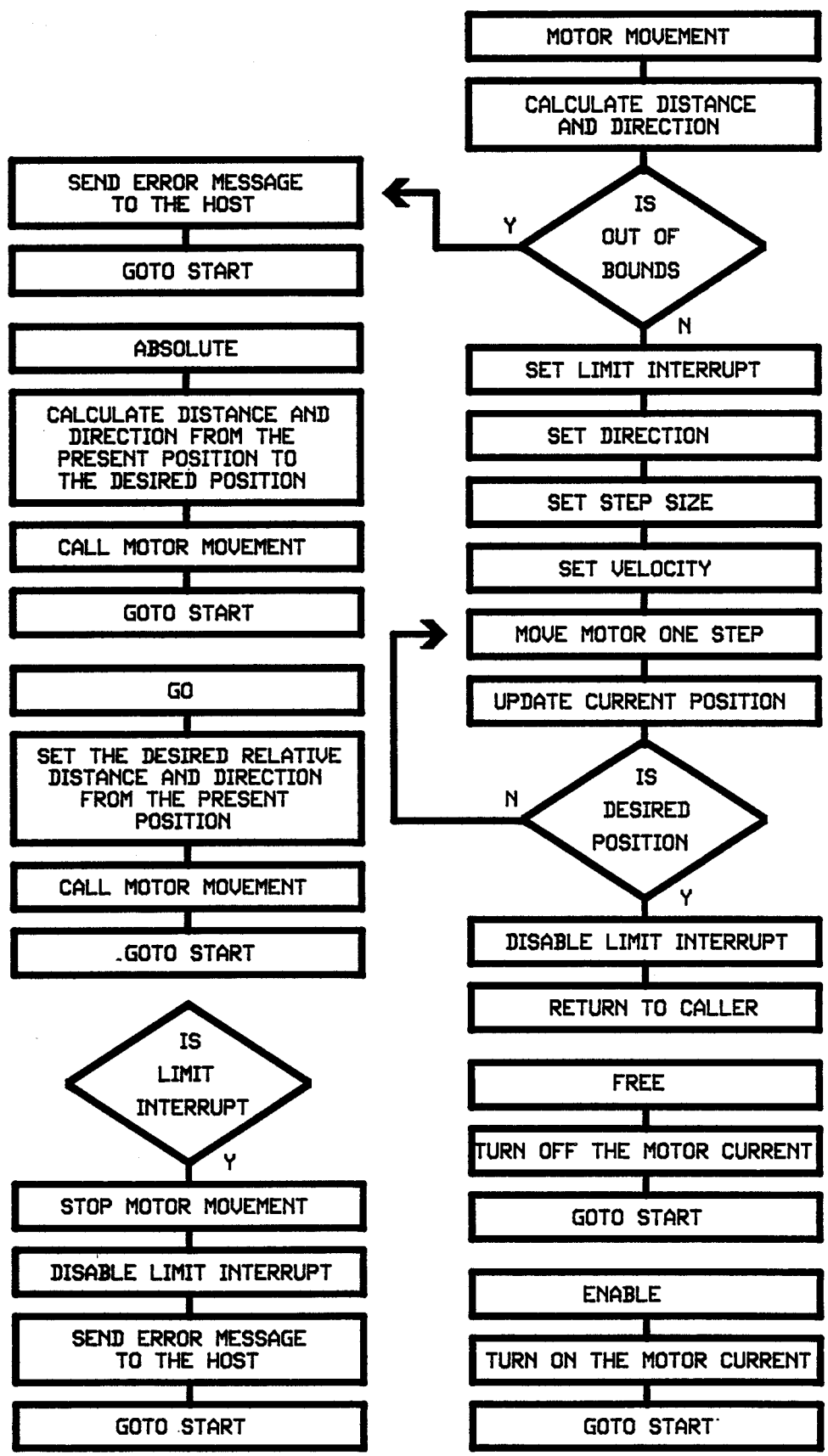

FIG. 1 shows an angled view of the readily demountable bracket 2 of the invention apart from the x-ray instrument of the prior art. Bracket 2 can be seen to comprise left side plate 30 and right side plate 32, attached to and defining the perpendicular ends to main bracket face plate 34. Each of left side plate 30 and right side plate 32 have two standoffs 36 for the purpose of affixing bracket 2 to x-ray instrument 14. The exact details of the standoffs 36 depend, of course, upon the exact physical configuration of the x-ray instrument 14, and are here depicted as a type of standoff particularly suited for the Philips-Norelco X-ray Instrument, used throughout for the purpose of illustrating the invention.

Within main bracket face plate 34 is perpendicularly mounted incrementally controlled motor 6, operably connected so that incrementally controlled motor gear pulley 22 extends within bracket 2 towards instrument 14. Perpendicularly affixed to main bracket face plate 34 and extending vertically therefrom is index limit detector bracket 26. On the far end of index detector bracket 26, adjacent the index mark 16 on x-ray instrument 14 is found optical interrupter 28, operably mounted so as to provide means for detecting the presence of index markers, described below. Both optical interrupter 28 and incrementally controlled motor 6 are interconnected electrically through computer cable 29 to computer interface plug 24, here a standard DB-15 plug. Computer interface plug 24 is wired so as to provide for separate computer interface signals for the detection function of optical interrupter 28 and separate signals providing phase currents to incrementally controlled motor 6. As is well understood in the art, typically there are four to eight such separate signal lines for a typical incrementally controlled motor 6 and four such lines for the two optical interrupters; the remaining lines being available for ground or for other ancilliary functions if desired.

As is understood in any typical x-ray instrument 14, the instrument is equipped with a manual control knob 50 for manually presetting the instrument to a specific given angle, reading the same off index mark 16 provided on the rotating shaft of the instrument. Since the instrument is also intended to be driven mechanically by a powered motor, internally installed, a separate parallel clutch drive shaft or manual shaft 18 is provided, interconnected through gearing to manual control knob 50.

This gear is removed and replaced with a suitable sized manual belt or chain driven gear pulley 52 mounted upon manual drive shaft 18. Drive belt 4 then operably interconnects incrementally controlled motor gear pulley 22 and driven gear pulley 52 for mutual rotation. It is understood that any non-slip flexible drive may be utilized, whether belt and pulley or chain and gear, and that either such is meant.

Optionally an idler gear pulley may be mounted, upon main bracket face plate 34; adjustment and fastening of an idler gear pulley so mounted on face plate 34, as by being fastened by motor mounting screws 38, provides a means for tensioning drive chain 4 so as to enhance operability of the rotational interconnection of incrementally controlled motor 6 and manual drive shaft 18.

Within any typical x-ray instrument 14 there will be found, connected to and extending from the index mark section 16 an indicia bracket 42; this is an elongated metal finger, part of the indexing system. A semi-cylindrical arc segment 44 is provided with a adapted mounting notch and plate 46, for enclosing indicia bracket 42 so that arc segment 44 rotates along its circumference in cooperation therewith.

Along and within arc segment 44 are found first and second arcuate slits 48 circumferentially extending along segment 44 in each of which are movably positioned limit pins 10 tightened by tightening means 11, such as a standard type nut. Limit pins 10 can thus be set to any desired position within slit 48 along the circumference of arc 44.

Inasmuch as arc 44 is directly connected to the rotational axis 58 of instrument 14, the position of limit pins 10 along the progressive movement of arc segment 44 therefore define a minimum and a maximum limit of angular rotation for the mechanism of instrument 14 about rotational axis 58.

Each of index marking pins 10 indicate the respective limit angular position by passing through two optical interrupters 28 thereby creating a computer compatible signal to indicate the respective level for the purposes of program control of the overall position of incrementally controlled motor 6. Two interruptors are used preferrable to sense both an occurrance of limit pin 10, as well as a direction of travel.

It is understood in the art that there are numerous methods of controlling incrementally controlled motor 6 utilizing both limit data and the characteristic that a uniform step of incrementally controlled motor 6 will produce a uniform angular increment within the instrument 14, this increment being a function of the relative gear pulley ratios of stepper gear pulley 22, manual driven gear pulley 52 and the design minimum angular step size for the given incrementally controlled motor 6. Further, the art understands that it is possible, with computer control, for incrementally controlled motor 6 to provide finer incremental positioning by synthesizing a partial stepper signal through digital to analogue circuitry. This is so-called microstepping, a known technique for increasing the precision of movement of the incrementally controlled motor 6 and thus of the instrument 14.

It can thus be seen that the apparatus comprises a readily installable or removable bracket and arc assembly, easily mounted to a instrument 14 without requiring internal modification or recalibration of the instrument 14 and readily settable to angular position by use of the movable calibratable index marks 10.

Thus, the apparatus of the invention permits a much more precise control and the ready adaption of a instrument 14 to computer control than the modifications of the prior art, without causing damage or irreversible modification to the instrument 14.

It should thus be apparent that the invention, while illustrated here in a specific model for a specific instrument, does in fact include those equivalents as are implicit in the claims.

I claim:

1. An externally mountable apparatus for adapting a manually settable x-ray defractometer for motor driven control comprising:
   a planar bracket, demountably affixed to the front of said instrument, proximate a manual control shaft thereof;
   incrementally controlled motor means affixed to said bracket;
   driven gear pulley means operably affixed to said manual control shaft; and
   drive means operably interconnecting said incrementally controlled motor and said driven gear pulley means for rotation;
   means for limiting angular rotation of said instrument.

2. An externally mountable apparatus for adapting a manually settable x-ray defractometer for motor driven control having a shaft for manual control thereof, comprising:
   a bracket removably affixed to the front of said instrument;
   a incrementally controlled motor operable supported upon said bracket;
   gear pulley means mounted upon said shaft for manual control for rotation thereof;
   a belt or chain drive operably interconnecting said incrementally controlled motor and said gear pulley means for rotation of said shaft for manual control;
   control means for controllably rotating said incrementally controlled motor; and
   means for creating a signal to said control means upon the rotation of said instrument to a first or a second angular limit.

3. The apparatus as described in claim 2 above further comprising:
   means, upon said bracket, for indicating the presence of a limit index means;
   a semi-circular arc, demountably affixed to a rotating position indicator upon said instrument;
   said arc rotating in a plane perpendicular to the axis of rotation of said instrument, in synchronization therewith; and
   a first and a second limit index means, slidably affixed along a circumferential line of said arc.

* * * * *